United States Patent
Zhang et al.

(10) Patent No.: US 11,955,765 B2
(45) Date of Patent: Apr. 9, 2024

(54) SYSTEMS AND METHODS FOR CONTROLLING LASER PULSING

(71) Applicant: Boston Scientific Scimed, Inc., Maple Grove, MN (US)

(72) Inventors: Jian James Zhang, Santa Clara, CA (US); Baocheng Yang, Fremont, CA (US); Xirong Yang, Fremont, CA (US); Hyun Wook Kang, Busan (KR); Brian Cheng, San Jose, CA (US); Peter Bull, San Jose, CA (US); Rongwei Jason Xuan, Fremont, CA (US); Thomas C. Hasenberg, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 277 days.

(21) Appl. No.: 17/032,061

(22) Filed: Sep. 25, 2020

(65) Prior Publication Data
US 2021/0098959 A1    Apr. 1, 2021

Related U.S. Application Data

(60) Provisional application No. 62/906,857, filed on Sep. 27, 2019.

(51) Int. Cl.
*H01S 3/091* (2006.01)
*A61B 18/26* (2006.01)
(Continued)

(52) U.S. Cl.
CPC ............ *H01S 3/0912* (2013.01); *A61B 18/26* (2013.01); *H01S 3/061* (2013.01); *H01S 3/092* (2013.01);
(Continued)

(58) Field of Classification Search
CPC ....... H01S 3/0912; H01S 3/092; A61B 18/26; A61B 2017/00154
See application file for complete search history.

(56) References Cited

U.S. PATENT DOCUMENTS

| 8,613,741 B1 | 12/2013 | Jones et al. |
| 2018/0092693 A1* | 4/2018 | Falkenstein ......... H01S 3/10038 |

FOREIGN PATENT DOCUMENTS

| DE | 10 2007 024111 | 12/2008 |
| FR | 2 906 091 | 3/2008 |
| FR | 2906091 | * 3/2008 |

OTHER PUBLICATIONS

International Search Report and Written Opinion issued in International Application No. PCT/US2020/052625, dated Dec. 9, 2020 (13 pages).

* cited by examiner

*Primary Examiner* — Michael Carter
(74) *Attorney, Agent, or Firm* — Seager, Tufte & Wickhem, LLP

(57) ABSTRACT

Techniques are provided for controlling an output laser pulse signal of a medical device. A control device defines a time duration of capacitive discharge to a laser device. The time duration corresponds to an intended energy of the output laser pulse signal. The control device generates a plurality of sub-pulse control signals. The sub-pulse control signals define a series of capacitive discharge events of the capacitor bank. The control device modulates one or more of a sub-pulse control signal period or a sub-pulse time duration of the sub-pulse control signals to modify the capacitive discharge of the capacitor bank to the laser device during the time duration.

7 Claims, 16 Drawing Sheets

(51) Int. Cl.
*H01S 3/06* (2006.01)
*H01S 3/092* (2006.01)
*H01S 3/16* (2006.01)
*A61B 17/00* (2006.01)

(52) U.S. Cl.
CPC ............ *H01S 3/161* (2013.01); *H01S 3/1643* (2013.01); *A61B 2017/00154* (2013.01)

SYSTEMS AND METHODS FOR CONTROLLING LASER PULSING

CROSS-REFERENCE TO RELATED APPLICATIONS

This patent claims the benefit of priority under 35 U.S.C. § 119 to U.S. Provisional Patent Application No. 62/906,857, filed Sep. 27, 2019, which is herein incorporated by reference in its entirety.

TECHNICAL FIELD

The present disclosure relates generally to medical systems, devices, and related methods. More specifically, the present disclosure relates to medical systems and/or devices for controlling laser pulsing for medical treatment.

BACKGROUND

Medical devices such as laser devices may be used to treat ailments in a patient. For example, laser devices may be used for lithotripsy to treat kidney stones in patients. Such laser devices may utilize pulsing techniques to deliver power to a treatment area. The power delivery may be governed by a control signal, which may control the discharge time of a capacitor and voltage to drive the laser pulsing.

Existing laser pulsing techniques are limited in the variety of pulse profiles that are available for application to a treatment area. For example, existing laser pulsing techniques may be limited by capacity discharge voltage, frequency and pulse energy, and thus, a laser output pulse shape may be highly non-uniform. In some examples, laser pulses may have high voltage overshoot problems with significant amplitude degradation over a pulse duration.

The systems, devices, and methods of the current disclosure may rectify some of the deficiencies described above, and/or address other aspects of the art.

SUMMARY

According to an example, a method is provided for controlling an output laser pulse signal of a medical device. The method may include defining, at a control device, a time duration of capacitive discharge of a capacitor bank to a laser device, where the time duration corresponds to an intended energy of the output laser pulse signal, generating a plurality of sub-pulse control signals that define a series of capacitive discharge events of the capacitor bank, and modulating one or more of a sub-pulse control signal period or a sub-pulse time duration of the sub-pulse control signals to modify the capacitive discharge of the capacitor bank to the laser device during the time duration.

The method may include one or more of the following aspects. In some example aspects, the time duration of the capacitive discharge may be modified by modifying the plurality of sub-pulse control signals. The time duration may be modified between a start of a first sub-pulse control signal and an end of a last sub-pulse control signal. The sub-pulse control signal period may correspond to the time elapsed between a start of the first sub-pulse control signal and a start of a subsequent sub-pulse control signal. The sub-pulse time duration may correspond to an elapsed time between a start of a selected sub-pulse control signal and an end of the selected sub-pulse control signal. The output laser pulse signal may be controlled by changing the time duration of the control laser pulse signal. The time duration of the control laser pulse signal may change to increase a peak output value time width of the output laser pulse signal. A frequency of the sub-pulse control signal may change to produce an output laser pulse signal with periodic peak output values. The sub-pulse control signals may have a frequency of about 1 kilo Hertz (kHz) to about 25 kHz.

The method may also include generating a plurality of sets of sub-pulse control signals. The method may include modulating a period of one or more of the sets of sub-pulse control signals or a time delay between subsequent sets of sub-pulse control signals to apply the control laser pulse signal during the time period. The method may also include modifying the time duration of capacitive discharge by modifying the plurality of sets of sub-pulse control signals. The time duration of capacitive discharge may correspond to an elapsed time between a start of a first sub-pulse control signal of a first set of sub-pulse control signals and an end of a last sub-pulse control signal of a last set of sub-pulse control signals. The method may also include modulating each set of sub-pulse control signals independently. The method may further include modulating an elapsed time between subsequent sets of sub-pulse control signals to produce an output laser signal with periodic peak output values.

In another example, a method may include controlling an output laser pulse signal of a medical device. The method may include defining, at a control device, a time duration of capacitive discharge of a capacitor bank to a laser device, where the time duration corresponds to an intended energy of the output laser pulse signal, generating a plurality of sets of sub-pulse control signals, each set defining a series of capacitive discharge events of the capacitor bank, and modulating a period of one or more of the sets of sub-pulse control signals or an elapsed time between subsequent sets of sub-pulse control signals to modify the capacitive discharge of the capacitor bank to the laser device during the time duration.

The method may include one or more of the following aspects. The method may include modifying the time duration of capacitive discharge by modifying the plurality of sets of sub-pulse control signals. The time duration of capacitive discharge may correspond to an elapsed time between a start of a first sub-pulse control signal of a first set of sub-pulse control signals and an end of a last sub-pulse control signal of a last set of sub-pulse control signals. The method may also include modulating each set of sub-pulse control signals independently. The method may further include modulating an elapsed time between subsequent sets of sub-pulse control signals to produce an output laser signal with periodic peak output values. A frequency of the peak output values may increase as the elapsed time between subsequent sets of sub-pulse control signals decreases.

In a further example, a control device may include an interface unit configured to send and receive control signals to a modulator system, a memory unit configured to store logic, and a processor configured to execute the logic. Executing the logic may cause the processor to define a time duration of capacitive discharge of a capacitor bank to a laser device, generate a plurality of sub-pulse control signals that define a series of capacitive discharge events of the capacitor bank; and modulate one or more of a sub-pulse control signal period or a sub-pulse time duration of the sub-pulse control signals to modify the capacitive discharge of the capacitor bank to the laser device during the time duration. The time duration may correspond to an intended energy of an output laser pulse signal.

The control device may include one or more of the following aspects. The processor may be configured to modify the time duration of capacitive discharge by generating a corresponding number of sub-pulse control signals. The sub-pulse control signal period may correspond to time elapsed between a start of the first sub-pulse control signal and a start of a subsequent sub-pulse control signal. The sub-pulse time duration may correspond to time elapsed between a start of a selected sub-pulse control signal and an end of the selected sub-pulse control signal. The processor may be further configured to control the output laser pulse signal by changing the time duration of the control laser pulse signal.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to systems, devices, and methods for controlling laser pulses of a medical device (e.g., a laser lithotripsy medical device). Reference will now be made in detail to examples of the present disclosure described above and illustrated in the accompanying drawings. Wherever possible, the same reference numbers will be used throughout the drawings to refer to the same or like parts.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

The terms "proximal" and "distal" are used herein to refer to the relative positions of the components of an exemplary medical device or medical insertion device. When used herein, "proximal" refers to a position relatively closer to the exterior of the patient or closer to a medical professional using the medical device or medical insertion device. In contrast, "distal" refers to a position relatively farther away from the medical professional using the medical device or medical insertion device, or closer to the interior of the patient.

Figure 1:
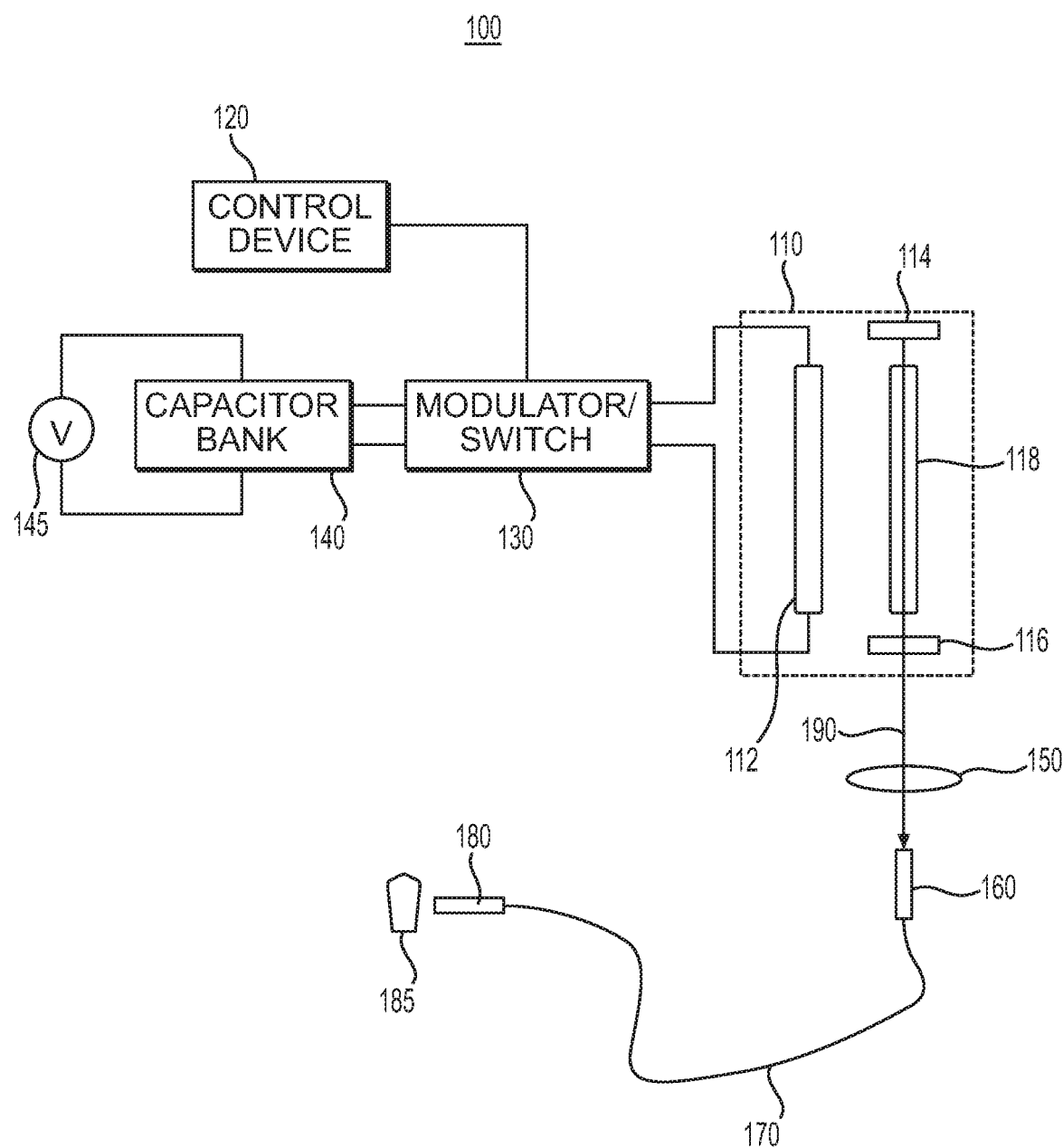
FIG. 1 illustrates an exemplary medical device in a schematic form including a laser cavity, a control device, and a modulator system to control laser pulsing for medical treatment, according to the present disclosure.

FIG. 1 schematically illustrates an example of a medical device for controlling laser pulsing. FIG. 1 shows the medical device at reference numeral 100. The medical device 100 (e.g., a laser device) includes a laser cavity 110, a control device 120, a modulator/switch system 130, a capacitor bank 140, a lens 150, and a laser delivery fiber 170 having a proximal fiber end tip 160, and a distal fiber end tip (e.g., a laser output) 180. FIG. 1 also shows a target for the medical device 100 at reference numeral 185. The target 185, for example, may be a kidney stone or may be a tissue within a patient for treatment by the medical device 100. The laser cavity 110 comprises several components, including a flash lamp 112, a first mirror 114, a second mirror 116, and a laser rod 118.

In one example, the medical device 100 may be a solid-state laser, such as a Holmium: yttrium-aluminum-garnet ("Ho: YAG") laser system. The Ho: YAG laser may be used for lithotripsy or other types of medical treatment. It should be appreciated that reference to a Ho: YAG laser is merely an example, and the laser control techniques described herein may be applicable to other laser systems or other solid-state lasers.

The control device 120, the modulator/switch ("modulator") system 130, and the capacitor bank 140 are located at a proximal end of the medical device 100. In one example, the control device 120, the modulator system 130, and/or the capacitor bank may be external or remote to the remainder of the medical device 100. The control device 120 is configured to communicate with the modulator system 130 to provide control signals (e.g., control laser pulse signals) to the modulator system 130, for example, to control output laser pulsing signals of the medical device 100, as described by the techniques herein. The modulator system 130 is configured to communicate with the capacitor bank 140, for example, to modulate the discharge output of the capacitor bank 140 and ultimately to provide electrical energy to the flash lamp 112, as described herein.

The capacitor bank 140 may comprise one or more capacitors. The capacitor bank 140 communicates with a voltage source 145. The voltage source 145 provides an electrical source to charge the capacitor bank 140. For example, based on the voltage applied by the voltage source 145 to the capacitor bank 140, the capacitor bank 140 may retain a corresponding capacitive charge for a period of time. The capacitor bank 140 may discharge at a certain frequency or over a certain period of time and may deliver electrical energy or power (e.g., electrical charge at a certain rate and/or at a certain energy level) to drive laser operations. The capacitor bank 140 discharge, thus, may control the laser pulsing of the medical device 100, e.g., the laser output of the medical device 100, as described by the techniques herein. In one example, the voltage source 145 is configured to be modulated (e.g., the voltage output of the voltage source is configured to be changed) by the modulator system 130.

The flash lamp 112 is configured to receive electrical signals (e.g., an electrical charge) from the capacitor bank 140 via the modulator system 130. For example, the modulator system 130 operates as a gate or a switch to transfer electrical energy from the capacitor bank 140 to the flash lamp 112. In one example, the control device 120 sends an on/off signal to the modulator system 130 which enables the capacitor bank 140 to transfer its stored charge to the flash lamp 112.

The flash lamp 112 may be a pumping flash lamp that is configured to optically pump a laser diode (e.g., the laser rod 118). For example, the flash lamp 112 may be supplied with electrical energy from the capacitor bank 140 via the modulator/switch system 130. The flash lamp 112 may operate to transfer energy from the capacitor bank 140 to the laser rod 118, e.g., to achieve atomic population inversion in the laser rod 118, thus ultimately achieving a stimulated emission output from the laser rod 118. The flash lamp 112, thus, may periodically supply ("pump" or "pulse") electrical energy to the laser rod 118 (e.g., an output laser pulse signal). The mirror 114 may be a high-reflection (HR) mirror to focus the flash lamp output into the laser rod 118. Likewise, the mirror 116 may be an output coupler (OC) configured to extract light from the laser rod 118 into an optical channel 190 for ultimate transmission to the delivery fiber 170. In one example, when the flash lamp 112 receives stored electrical energy from the capacitor bank 140 (e.g., as the capacitor bank 140 discharges), the flash lamp 112 pulses accordingly, and the released light energy is absorbed by the laser rod 118 which, together with mirrors 114 and 116, generates a laser pulse output.

The laser pulse output travels through the optical channel 190 and is focused by the lens 150 to the proximal fiber end tip 160. The laser pulse then travels through the delivery fiber 170 to the distal fiber end tip output (e.g., laser output) 180 for ultimate delivery to the target 185 (e.g., a stone or a tissue), which is proximate the laser output 180. The reaction of the target 185 to the laser pulse results in the desired effects (e.g., the desired treatment outcome). It should be appreciated that the medical device 100 in FIG. 1 is merely an example, and the laser system may include more than one laser cavity.

In general, laser systems that utilize a flash lamp (such as flash lamp 112) to pump or pulse electrical energy to a laser rod (e.g., laser rod 118), e.g., as described above may be referred to as "flash pumped laser systems." In typical flash lamp-pumped laser systems, the discharging process of electrical energy from the capacitor bank 140 to the flash lamp 112 is affected by multiple factors. For example, the discharge process is affected by the stored energy of the capacitor bank 140, switching behavior of the modulator system 130, and specific flash lamp properties. Thus, the current (e.g., charge) transferred between the capacitor bank 140 and the flash lamp 112 is not a constant current transfer. Additionally, the conversion from electrical energy to a final laser pulse energy (e.g., the transfer of the pulsing of the flash lamp 112 to the laser rod 118) is also a non-linear process. Thus, the temporal evolution of the laser pulse (e.g., how the laser output pulse signal of the laser rod 118 changes over time) is not a linear response to the control signal sent by the control device 120 to the modulator system 130 for discharging the capacitor bank 140. In some examples, the laser output of the laser rod 118 is eventually determined by the coding of the control signals of the modulator system 130. The techniques herein describe techniques for delivering control signals from the control device 120 to the modulator system 130 for discharging the capacitor bank 140 in order to obtain more versatile output laser pulse signals from the laser rod 118 and ultimately from the medical device 100 to the target 185.

Figure 2A:
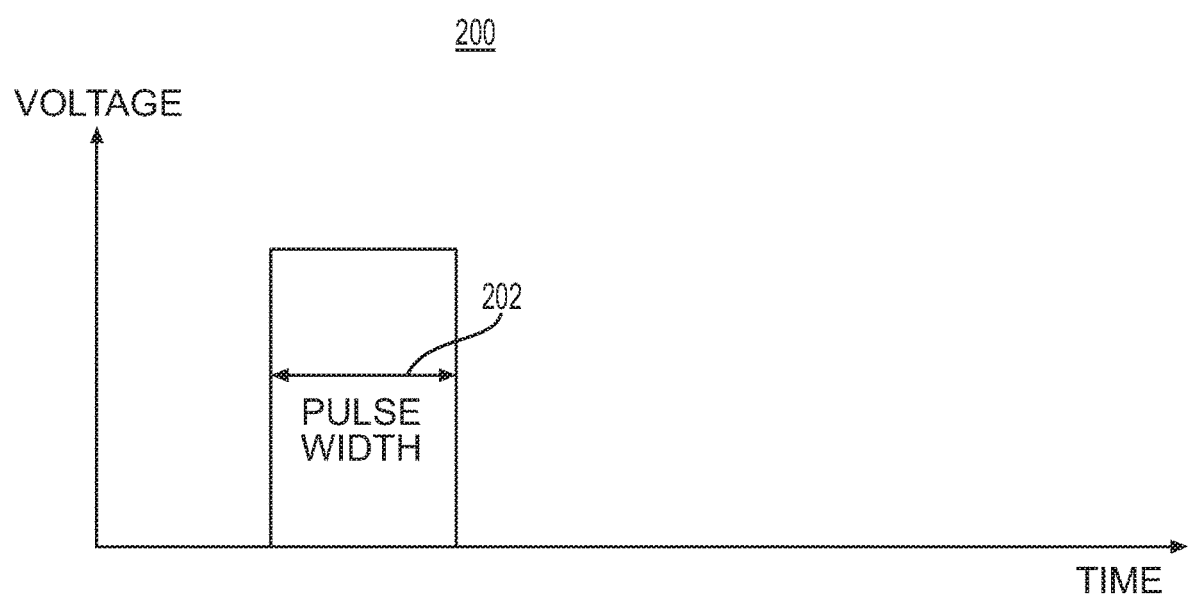
FIG. 2A and 2B illustrate example graphical representations of a control laser pulse signal and a corresponding output laser pulse signal.

Reference is now made to FIG. 2A, which shows a conventional pulsing mode for medical device 100. FIG. 2A specifically shows a graphical representation 200 of a control signal generated by the control device 120 for the capacitive discharge of the capacitor bank 140 (e.g., via the modulator system 130). In FIG. 2A, the control signal is a rectangular shaped signal pulse repeated at a repetition rate of the laser pulse. The pulse width 202 of the control signal determines how long the discharging of the capacitor bank 140 will last for the given voltage amplitude of the electrical pulse. In other words, in FIG. 2A, when the voltage magnitude is fixed for the capacitor bank 140, the control signal will dictate how long the capacitor bank 140 will discharge for that fixed voltage magnitude. In this example, though the actual discharging process of the capacitor bank 140 is not a linear response of the control signal pulse shape (e.g., the output laser pulse in response to the control signal will not map directly to the control signal), the total energy of the generated output laser pulse is directly controlled and adjusted by the width and the set voltage of the control signal pulse. When the voltage is fixed, changing the pulse width 202 of the control signal can change the output laser pulse energy, and thus, if a specific energy level is desired for the output laser pulse profile directed at the target 185, a fixed voltage restricts the ability for the pulse width 202 to change, since changing the pulse width 202 will affect the laser pulse energy. For example, in this conventional embodiment, if a wider pulse width is required (e.g., a longer capacitive discharge time), the voltage magnitude has to be lowered to maintain a specific laser output energy level.

Figure 2B:
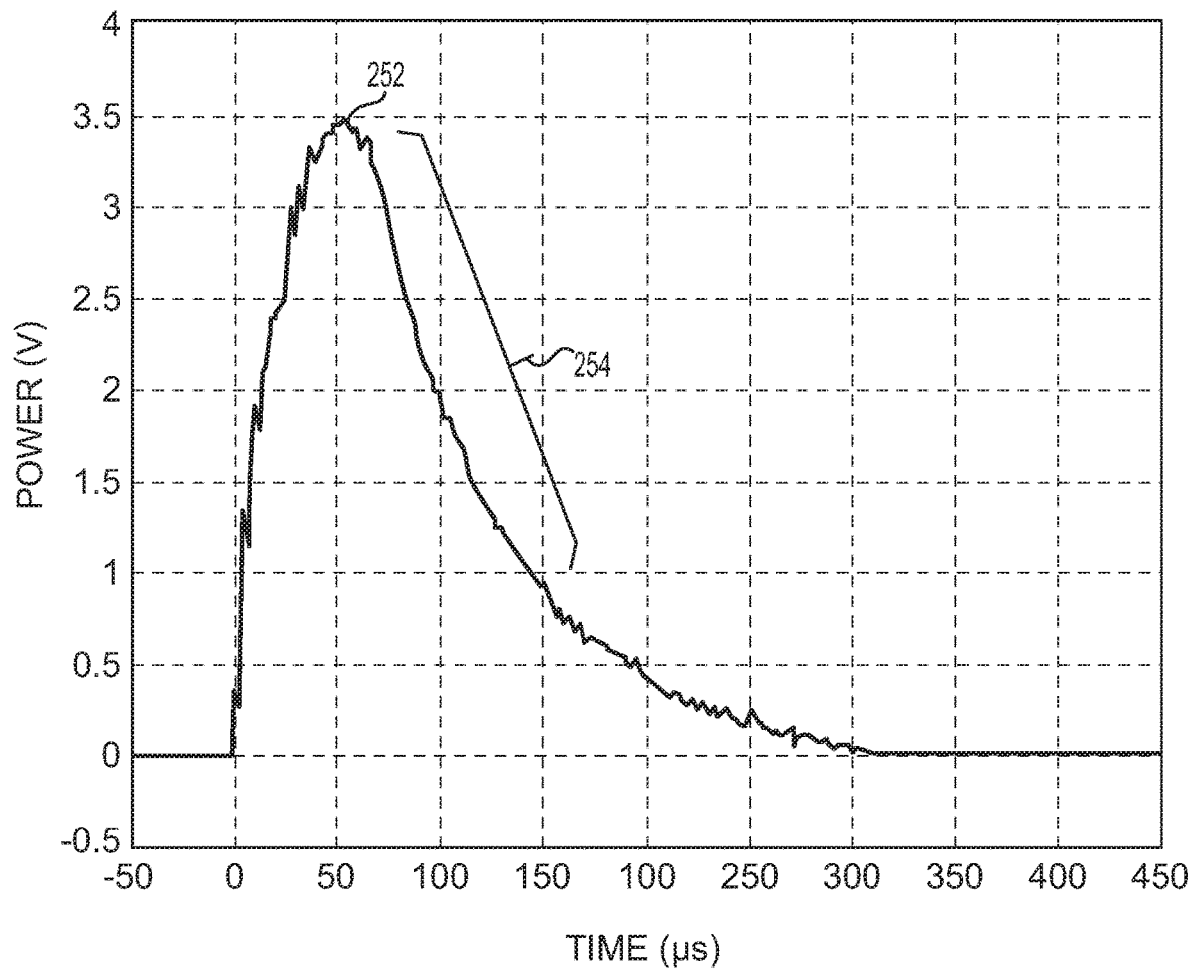

FIG. 2B shows, at 250, the temporal shape of the laser output for the conventional control signal 200. The techniques of applying the conventional control signal 200 have several limitations. For example, as stated above, pulse width modifications are limited for fixed voltages. As a result, the laser output 250 is generally narrow (or "short"). Additionally, as shown in FIG. 2B, the laser output 250 has a peak output value, at 252, and quickly degrades over a large continuous slope, as shown at 254. These limitations, among others, may be overcome by the techniques described herein.

For clarity, it should be appreciated that the terms "control signal," "control laser pulse signal," "control laser pulsing signal," and/or "control pulse" may be used interchangeably herein and may refer to a signal generated by the control device 120 to control a laser output of the medical device 100. Likewise, it should be appreciated that the terms "output signal," "output laser pulse signal," "output laser pulsing signal," "output laser pulse profile," "output laser pulsing profile," "output laser pulse train," and/or "output laser profile" may be used interchangeably herein and may refer to the laser signal output from the medical device 100 (e.g., in response to or corresponding to a control signal) for treatment to the target 185. In some examples, the control signal is a digital signal, and the output signal is an analog signal.

Figure 3A:
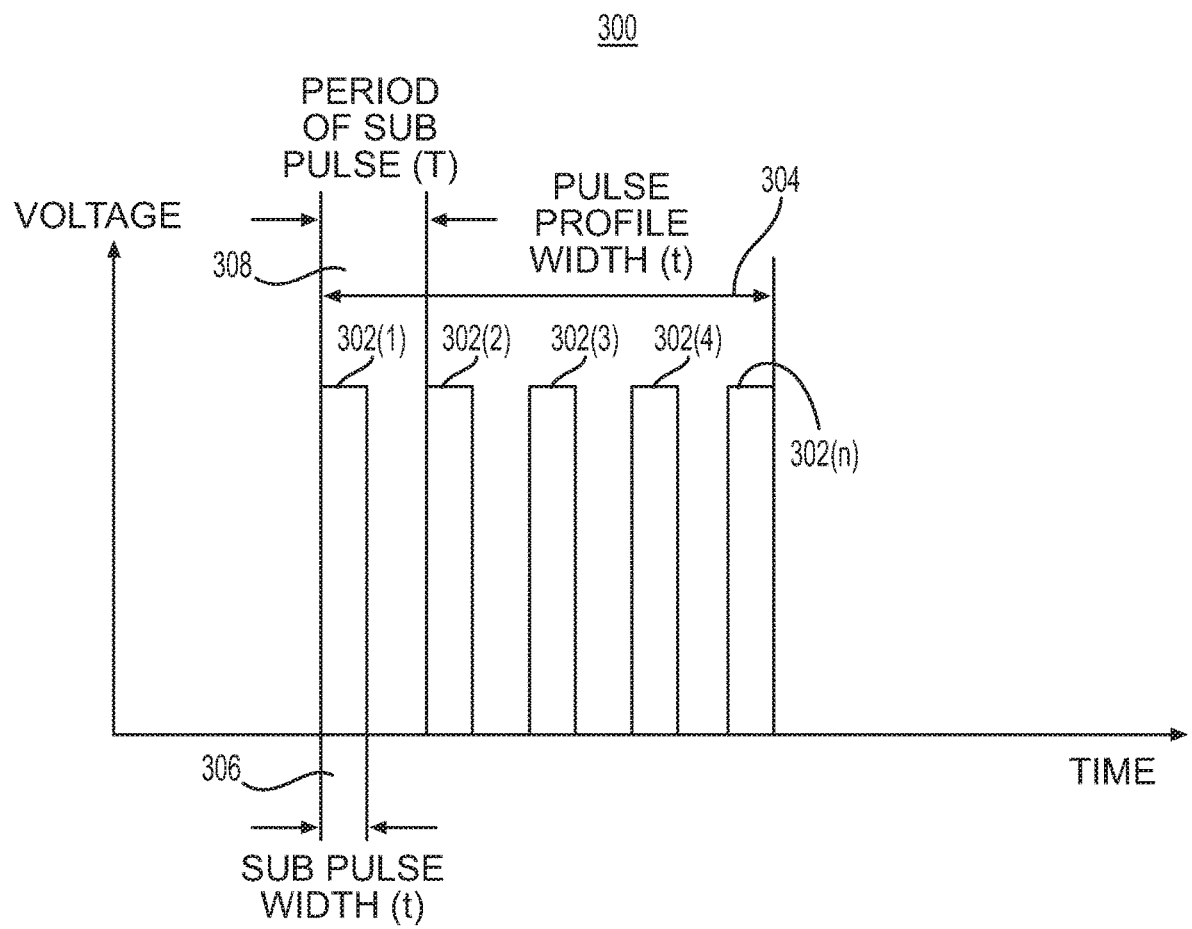
FIGS. 3A-3E illustrate other example graphical representations of a control laser pulse signal and corresponding output laser pulse signals using pulse-width modulation and pulse-width tailoring techniques.

Reference is now made to FIG. 3A. FIG. 3A shows a graphical representation 300 of a first technique of modifying a laser pulse control signal to generate a desired output laser signal. In FIG. 3A, the laser pulse control signal 300 comprises a plurality of sub-pulses, shown at 302(1)-302(n). Each sub-pulse is a single "burst" control signal for discharging the capacitor bank 140. For example, sub-pulse signal 302(1) may be a first control signal generated by the control device 120, sub-pulse signal 302(2) may be a second single control signal generated by the control device 120, and so on. Thus, in FIG. 3A, the laser pulse control signal 300 is a combination of a plurality of single "burst" control signals (e.g., a combination of the sub-pulse signals 302(1)-302(n)). The control device 120 is thus able to more robustly control the pulse profile width of the laser pulse control system 300 by generating any number of sub-pulse control signals to achieve a desired pulse profile width. In FIG. 3A, the pulse profile width is shown at reference numeral 304, which comprises the time duration between the start of the first sub-pulse signal 302(1) and the end of the last sub-pulse signal 302(n). Each sub-pulse has its own sub-pulse width (e.g., "duty cycle"), shown at reference numeral 306. The overall pulse profile width 304 may be extended by modulating the period of the sub-pulse, shown at reference numeral 308. For example, the pulse profile width 304 can be extended by increasing the period of the sub-pulse 308 (e.g., the time distance between the start of consecutive sub-pulses) and can be contracted by decreasing the period of the sub-pulse 308. This type of modulation is referred to herein as pulse-width modulation ("PWM"). One example advantage of PWM is if "kick on" pulses are needed for the operation of the medical device 100 (e.g., low energy laser outputs), sub-pulses with relatively low voltage magnitudes may be added and adjusted easily. For traditional laser output, the period of the sub-pulse 308 may be relatively small (e.g., around 50 microseconds) corresponding to a PWM of (20 kilo-Hertz (kHz)).

The overall pulse profile width 304 may also be extended by modulating each individual sub-pulse one by one. For example, the sub-pulse width 306 may be modified for each sub-pulse (e.g., to expand or contract each sub-pulse). Thus, the sub-pulses 302(1)-302(n) may be modulated by tailoring each sub-pulse. These techniques are called pulse-width tailoring (PWT). PWT may result in sub-pulses 302(1)-302(n) that are uniform or non-uniform with each other, as required.

Figure 3B:
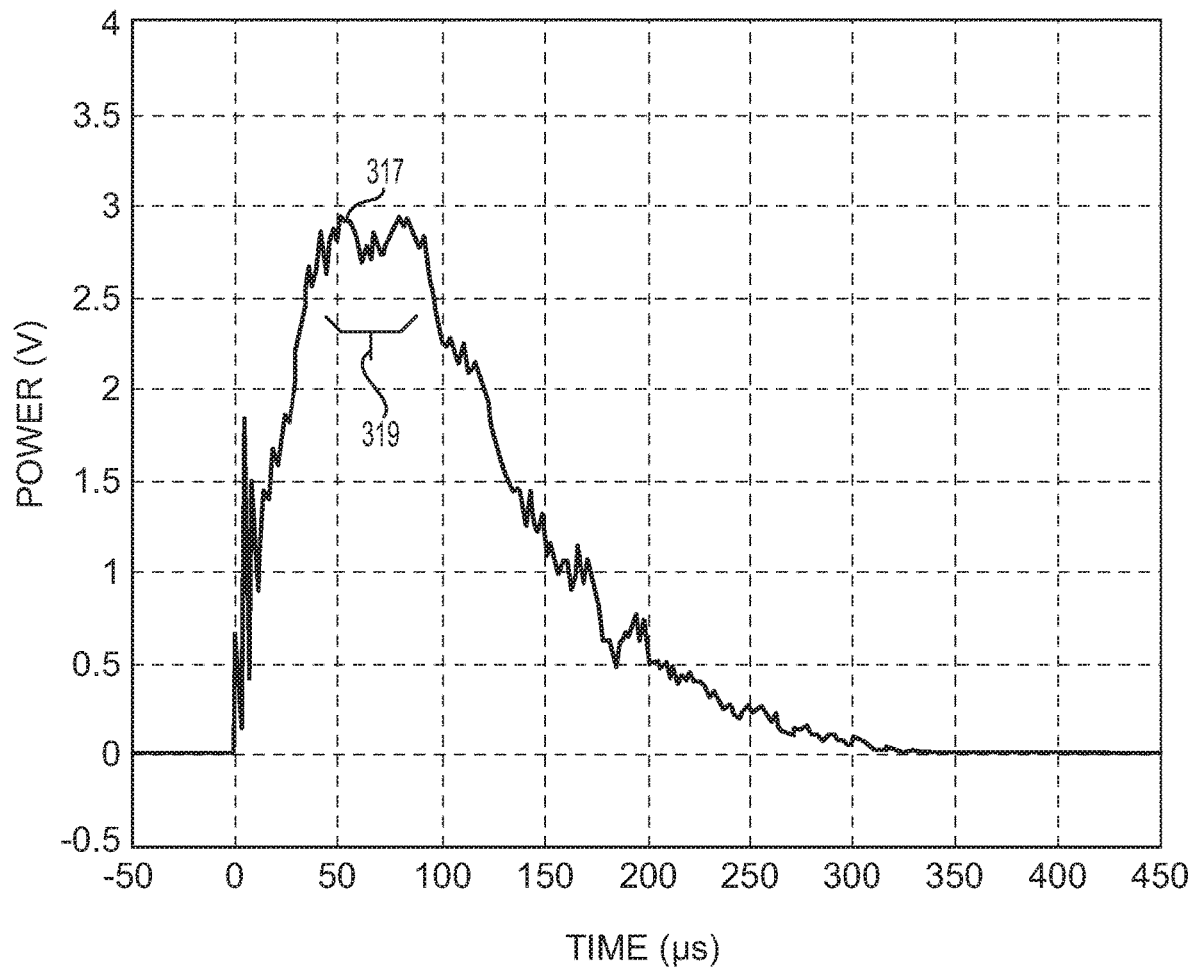

Reference is now made to FIGS. 3B-3E, which show example graphical representations of output laser pulse profiles based on the modulation and tailoring techniques described in connection with FIG. 3A. For example, for a similar pulse frequency as in FIGS. 2A and 2B (e.g., 20 kHz or higher), FIG. 3B shows a graphical representation 315 where the peak output value 317 of the laser output is reduced relative to the peak output value 252 shown in FIG. 2B, with a longer pulse width, shown at reference numeral 319, relative to the pulse width of the peak output value 252. In other words, for similar laser operating conditions, the control signal in FIG. 3A results in a longer duration output laser pulse at or near the peak output value 317 than the control signal in FIG. 2A.

Figure 3C:
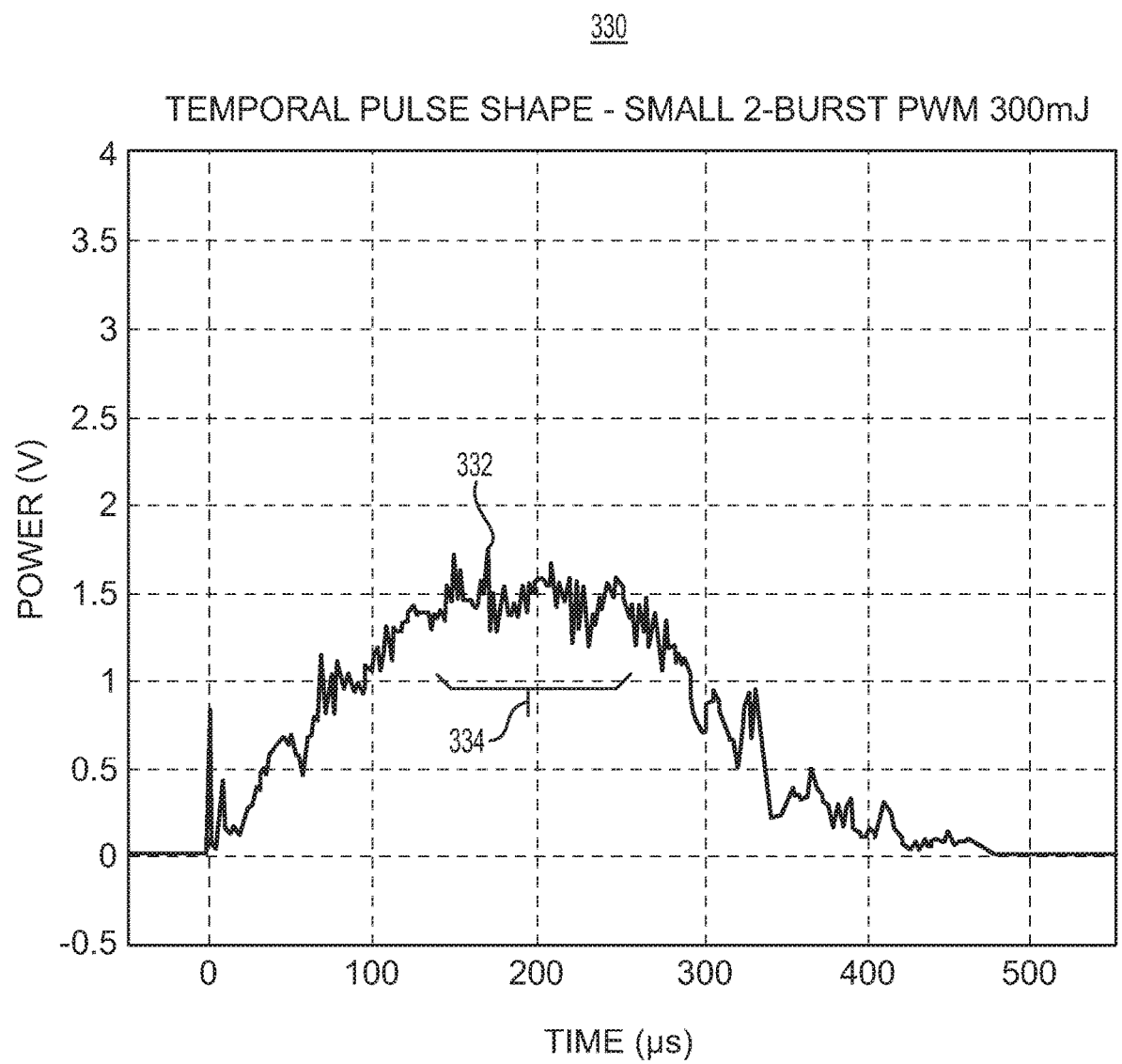

FIG. 3C shows a graphical representation 330 of the output laser profile with the pulse profile width 304 being increased using PWM techniques (e.g., a pulse width of about 450 microseconds and a sub-pulse frequency of about 25 kHz). The output laser profile 330 has a lower peak output value of 332 than the peak output value 317 in FIG. 3B and the peak output value 252 in FIG. 2B, but the output pulse width of 334 is longer.

Figure 3D:
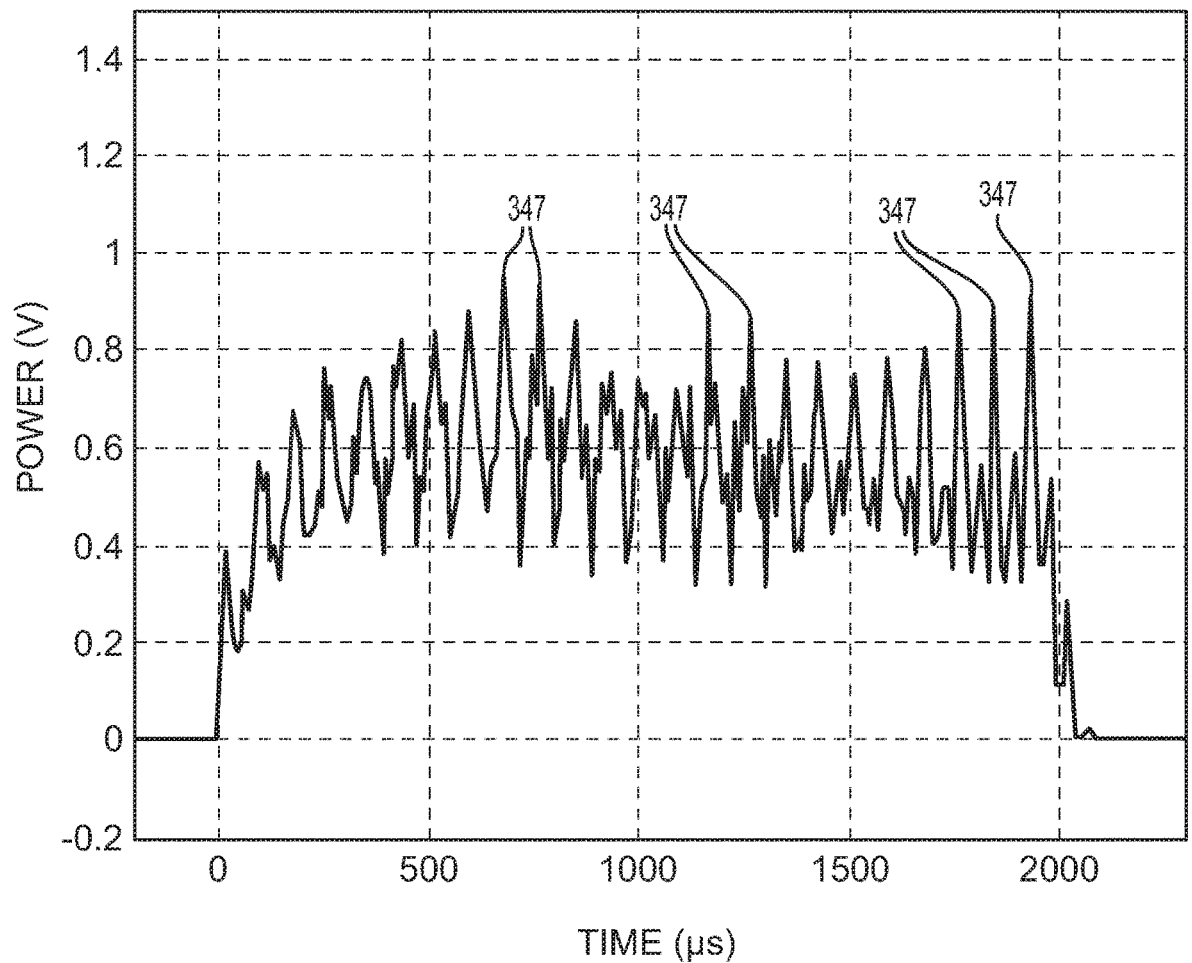

When the frequency of the sub-pulses 302(1)-302(n) (e.g., "sub-frequency") is in a moderate range (e.g., from about 8 kHz to 20 kHz), the resulting laser output pulses may become what is referred to as "dust mode" laser pulses. Dust mode laser pulses may be applied, for example, to kidney stones to break up the kidney stone into a powder or dust during lithotripsy. The dust mode output laser pulses are shown in FIG. 3D at reference numeral 345. In this example, PWM or PWT may be applied to the sub-pulses 302(1)-302(n), and the corresponding peak output values 347 of the output laser pulse profile 345 may be pronounced.

Figure 3E:
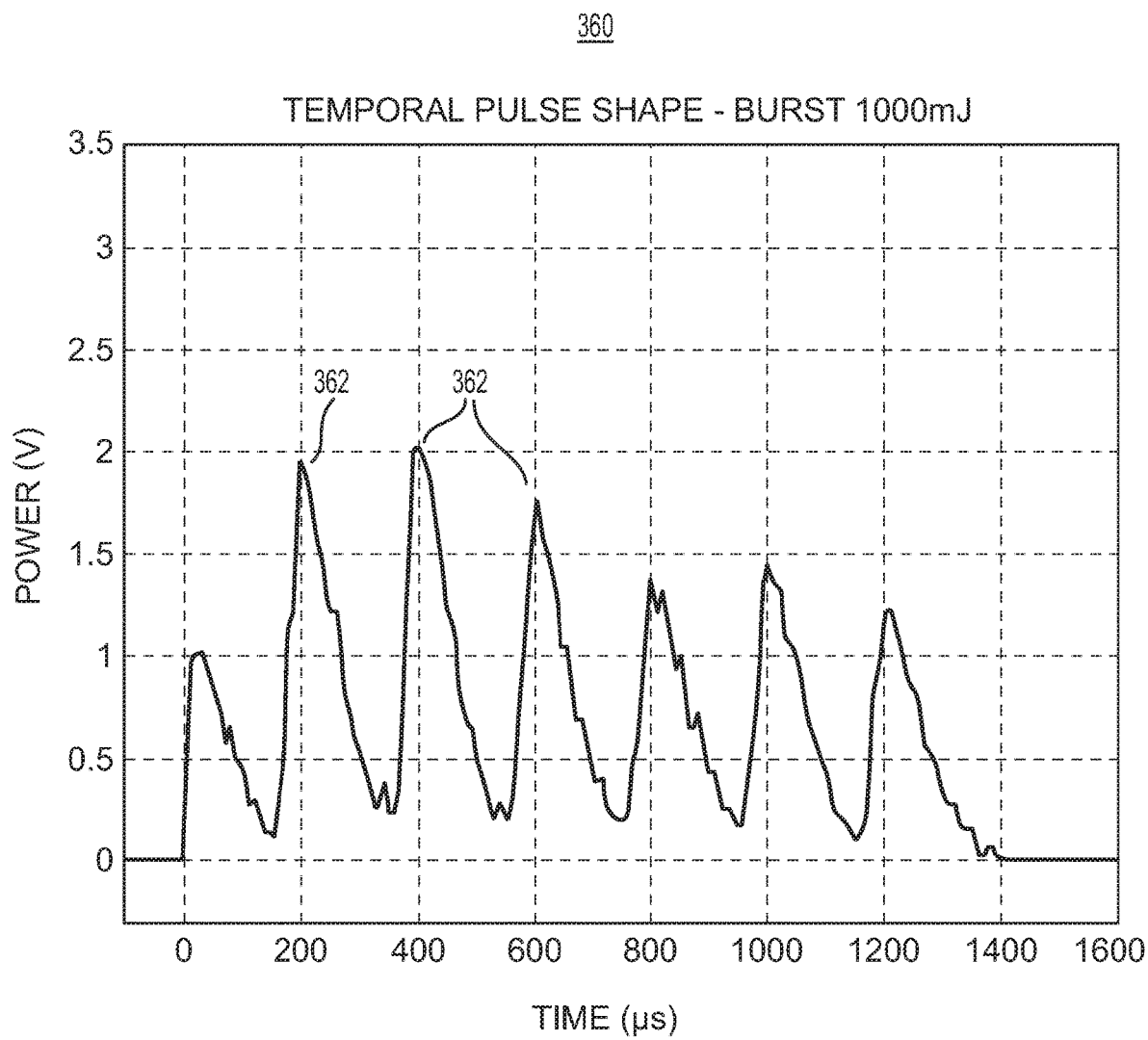

FIG. 3E shows an example graphical representation of the output laser pulse profile at 360 where the sub-frequency is further reduced (e.g., 8 kHz or lower). In this example, the laser pulses will become burst pulses, as shown in reference numeral 362. In this example, due to the low sub-frequency, the sub-pulses 302(1)-302(n) are well separated from one another.

Figure 4A:
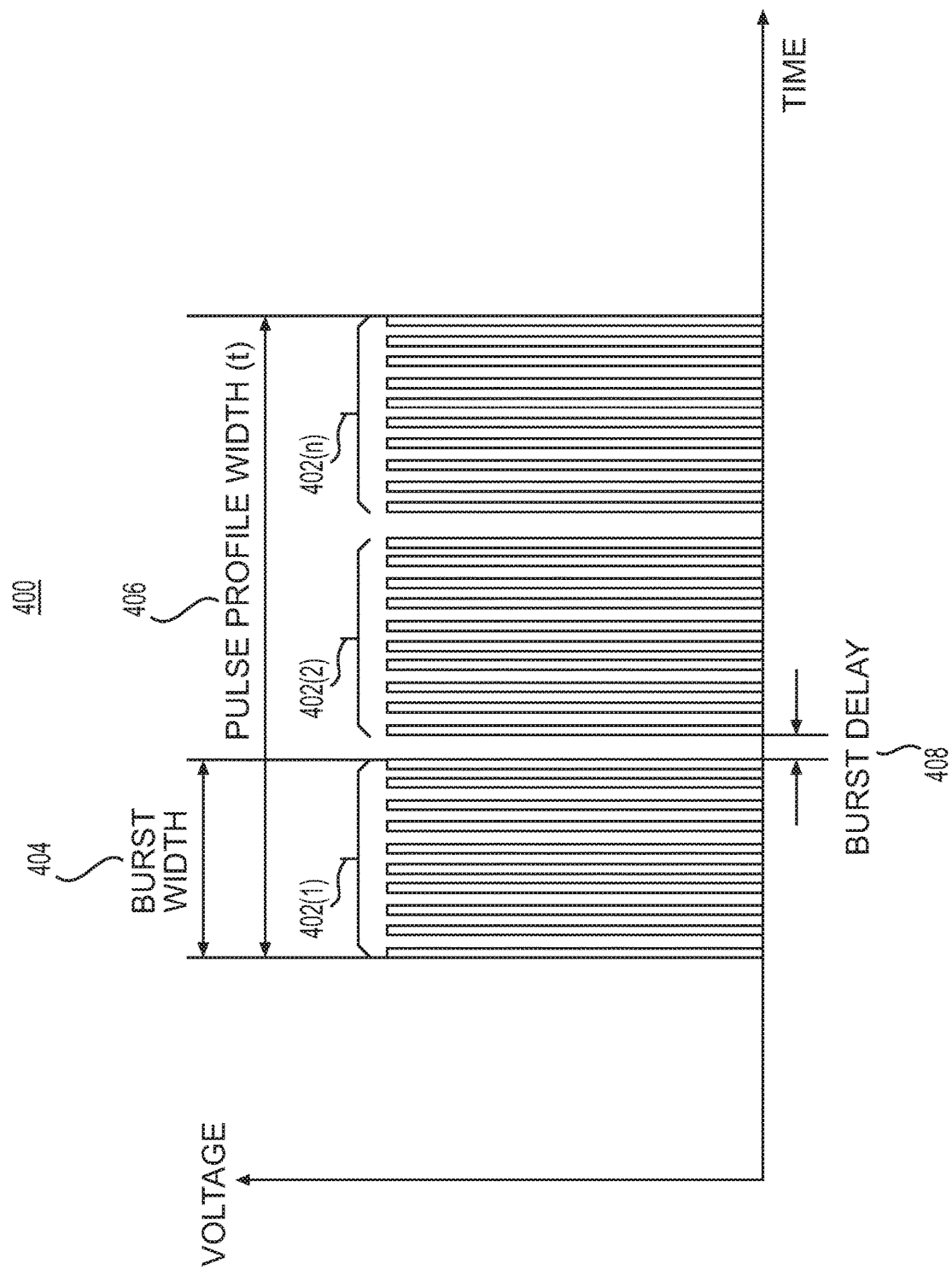
FIGS. 4A-4E illustrate further example graphical representations of a control laser pulse signal and corresponding output laser pulse signals for sets of sub-pulse control signals and sub-pulse burst delays.
Figure 4B:
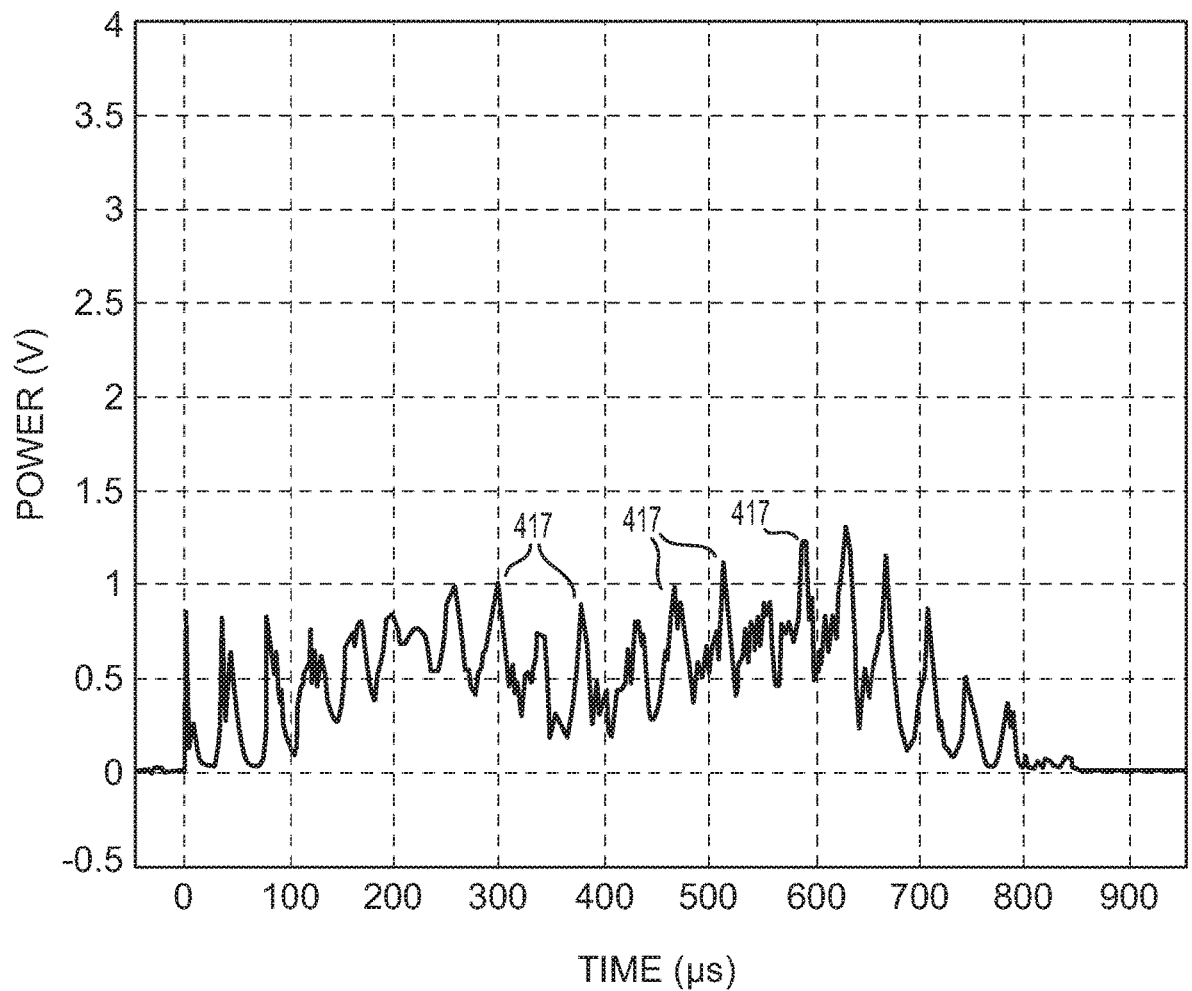
Figure 4C:
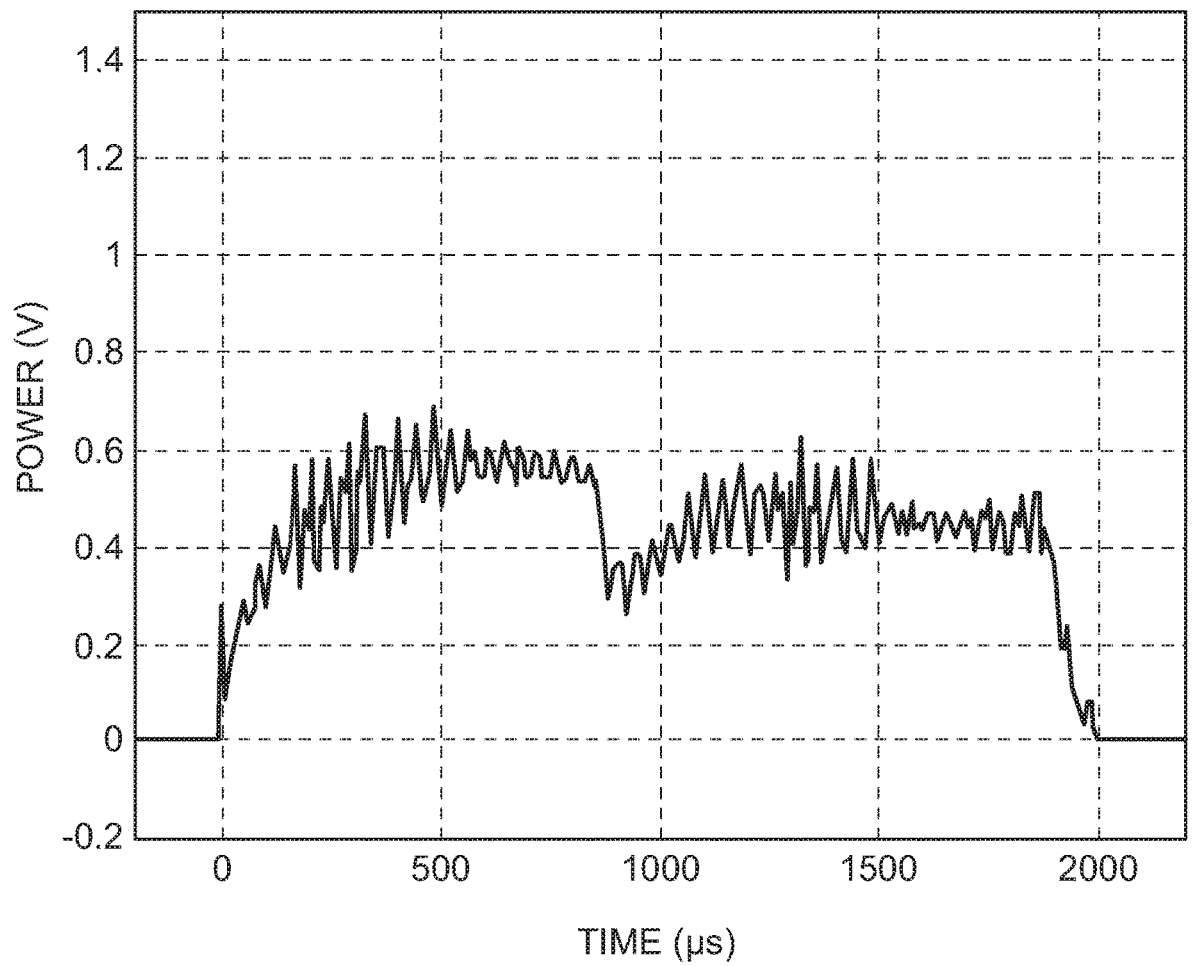
Figure 4D:
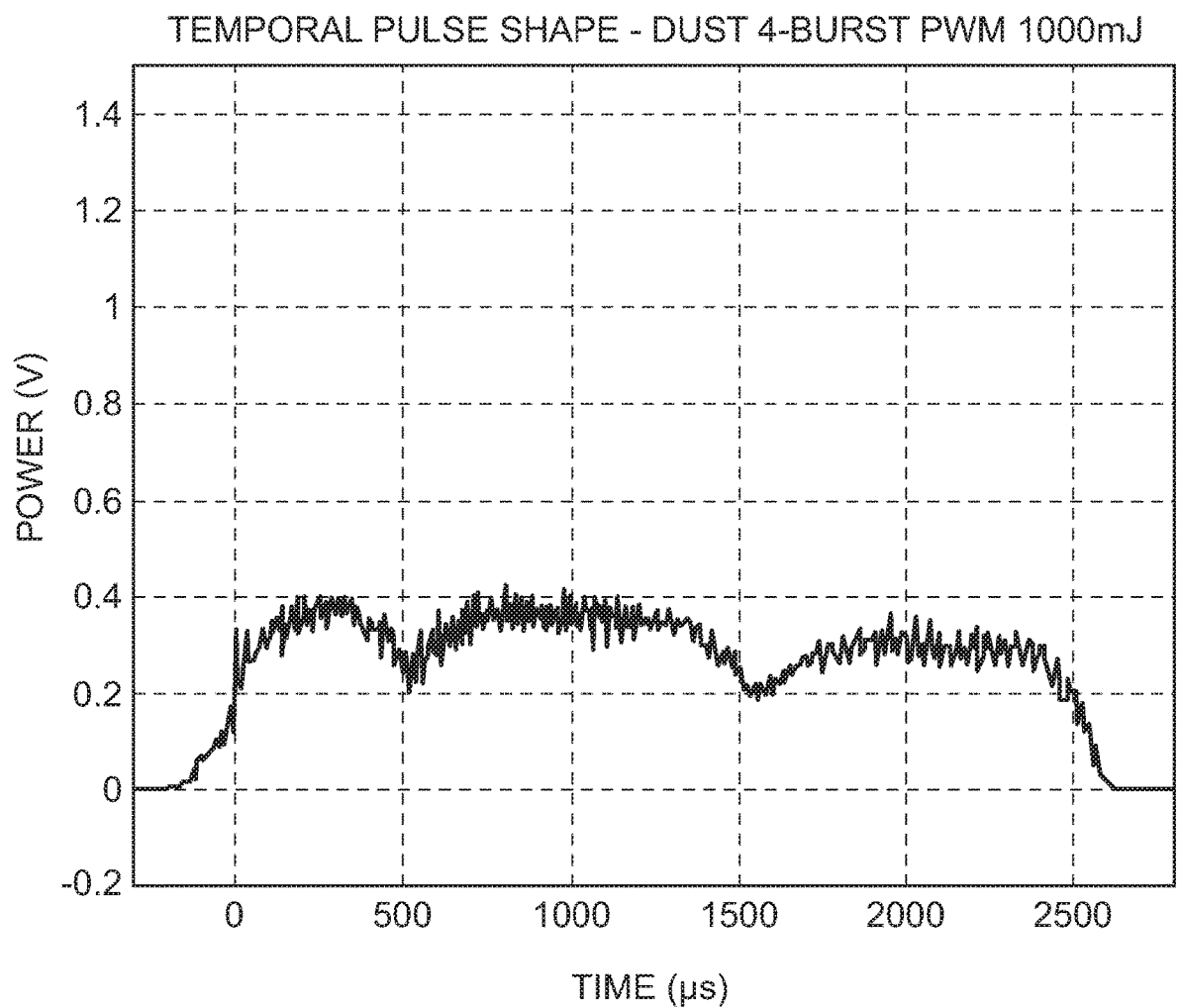
Figure 4E:
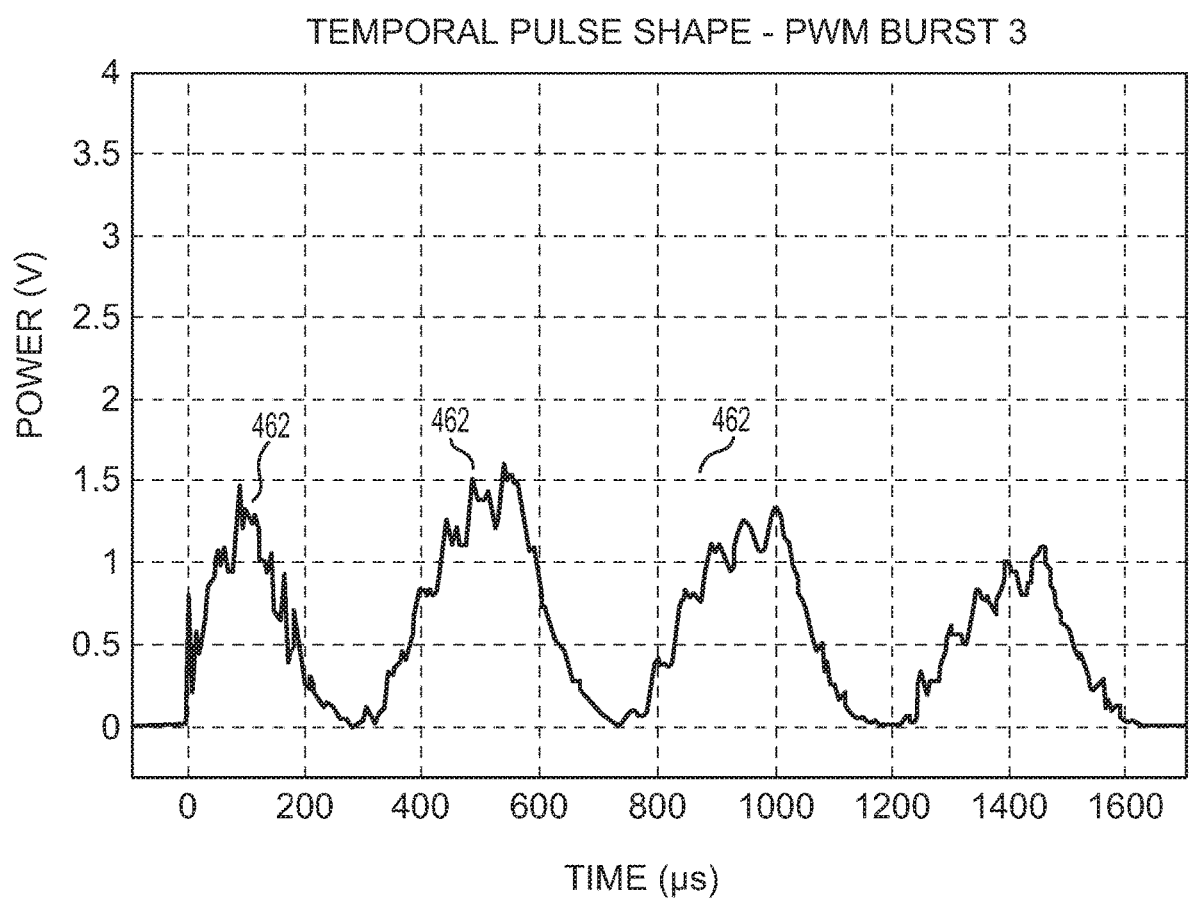

Reference is now made to FIG. 4A. FIG. 4A shows a graphical representation 400 of another technique of modifying a laser pulse control signal to generate a desired output laser signal. In FIG. 4A, the laser pulse control signal 400 comprises a plurality of sets of sub-pulse bursts, shown at reference numeral 402(1)-402(n), to form the overall laser pulse control signal 400. In one example, the overall laser pulse control signal 400 is formed by a combination of PWM and PWT techniques, as described above. For example, a first set of sub-pulse bursts is defined according to the PWT techniques of pulse definition. Sub-pulses are then further defined with the PWM scheme. The laser pulse control signal 400 may also be referred to as a combined PWM-burst pulse control signal. FIG. 4A shows a burst width 404 for each set of sub-pulse bursts, and an overall pulse profile width 406 for the laser pulse control signal 400. FIG. 4A also shows a burst delay 408 that represents a time differential between sub-pulses bursts. In one example, as shown at 415 in FIG. 4B, if the burst delay 408 is relatively small, the control signal 400 will generate an output laser pulse signal with periodic peak output values, as shown at reference numeral 417 in FIG. 4B. The peaks may increase in frequency as the burst delay 408 decreases in time duration (e.g., elapsed time). These are shown as "dust mode" pulses, shown at reference numeral 430 in FIG. 4C and reference numeral 445 in FIG. 4D. FIG. 4E shows the output laser pulse profile 460 when PWM modulation is applied on the burst pulse control signal 400 (e.g., resulting in a PWM-burst pulse control signal). In FIG. 4E, the peak output values 462 are relatively low, but the output laser pulse profile 460 has a wider temporal width (e.g., time duration).

Figure 5:
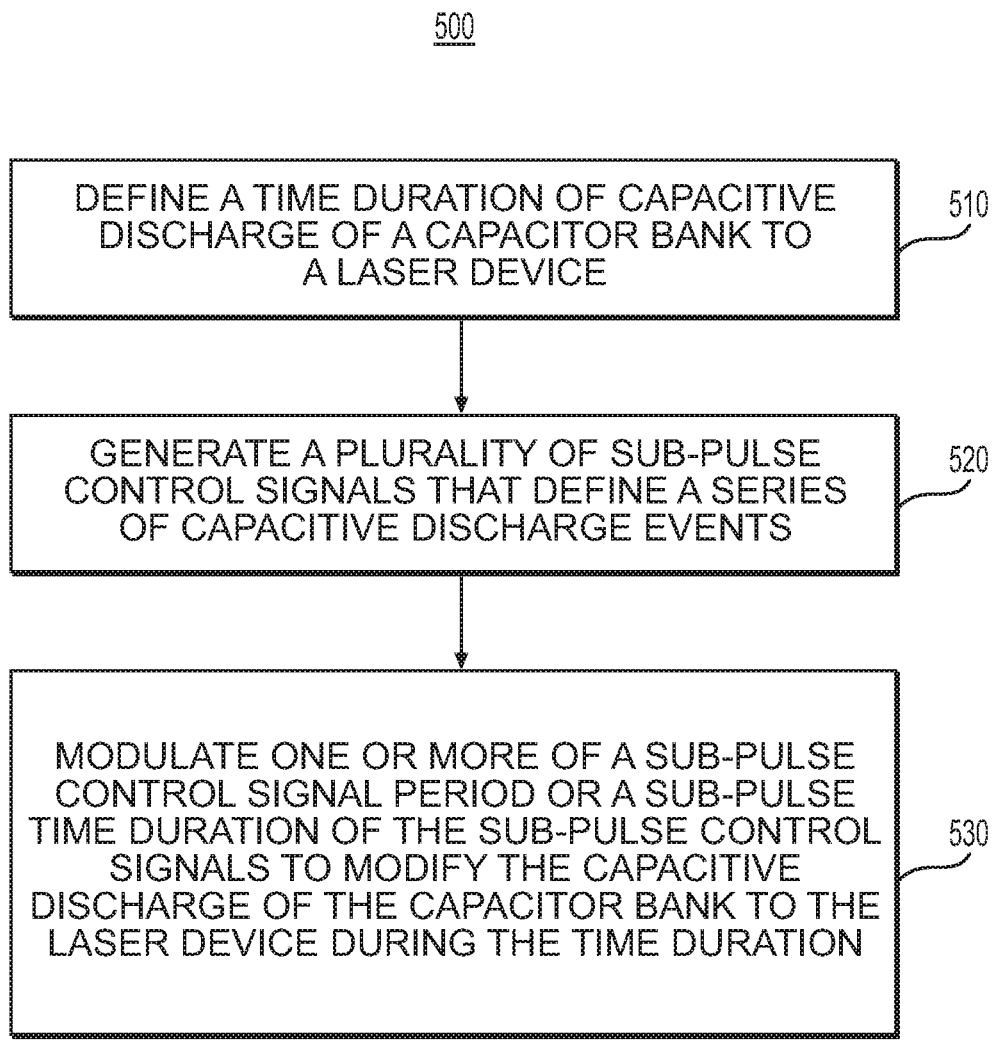
FIG. 5 shows a first example flow chart for controlling output laser pulse signals.

Reference is now made to FIG. 5, which shows a first example flow chart 500 for controlling output laser pulse signals. The operations in flow chart 500 may be performed by the control device 120. In one example, it should be appreciated that the operations performed by the control device 120 may be initiated and/or controlled by an operator of the control device 120 (e.g., by the operator providing input signals to the control device or otherwise initiating or controlling the control device 120). For example, a human operator (such as a medical professional administering the treatment of the target 185) or a computer operator (such as an automated program) may set operating parameters of the control device 120 (e.g., the control signals) to achieve an output signal desired by the operator.

In one example, the operator may seek a desired output signal and may program or otherwise operate the control device 120 to generate control signals to ultimately achieve the desired output signal. At 510, the control device 120 defines a time duration (e.g., sets or established a desired time duration) of capacitive discharge for an application of a control laser pulse signal to a laser device. The control device 120 defines the time duration of the capacitive discharge based on the intended output laser pulse signal desired for the medical device 100. For example, the control device 120 may define a first-time duration to achieve an output laser signal operating at a first corresponding energy for medical treatment on the target 185. In one example, the operator (described above) may determine an intended time duration of capacitive discharge based on a desired output signal, and the time duration set or established by the operator may be stored in a memory of the control device 120. In another example, the control device 120 itself may determine the intended time duration of capacitive discharge by receiving instructions from the operator on the intended output signal and by executing logic stored in the memory to set parameters, such as a time duration of capacitive discharge and other parameters described herein, of the control signal to achieve the intended output.

At 520, the control device 120 generates a plurality of sub-pulse control signals. In one example, the sub-pulse control signals may be generated by the control device 120 as it executes logic stored in memory to achieve the desired output signal. In another example, the sub-pulse control signals may be generated at the instruction of the operator (e.g., the operator may instruct the control device 120 to generate specific sub-pulse control signals). The plurality of sub-pulse control signals defines a series of corresponding capacitive discharge events from the capacitor bank 140. For example, a first sub-pulse control signal defines a first discharge event from the capacitor bank 140 over a first elapsed time, a second sub-pulse control signal defines a second discharge event from the capacitor bank 140 over another elapsed time, and so on. The aggregate of the elapsed time of the plurality of sub-pulse control signals comprises the time duration defined by the control device. The sub-pulse control signals are sent by the control device 120 to the modulator system 130, which operates the discharge of the capacitor bank 140 (e.g., by operating a switch interfaced with the capacitor bank 140) for a specified time defined by each of the sub-pulse control signals.

At 530, the control device 120 modulates one or more of a sub-pulse control signal period or a sub-pulse time duration of the sub-pulse control signals to apply the control laser pulse signal during the time duration. In one example, the operator may send instructions to the control device 120 for the control device 120 to modulate the one or more sub-pulse control signals. For example, the operator may intend to change the signal characteristics of the output signal and may instruct the control device 120 to modulate the control signals accordingly to achieve the newly desired output signal. In another example, the control device 120 may modulate the sub-pulse control signals automatically based on instructions from the operator to modify or otherwise change the intended output signal. The modulated signal is sent from the control device 120 to the modulator system 130 to modify/modulate the capacitive discharge of the capacitor bank 140.

Figure 6:
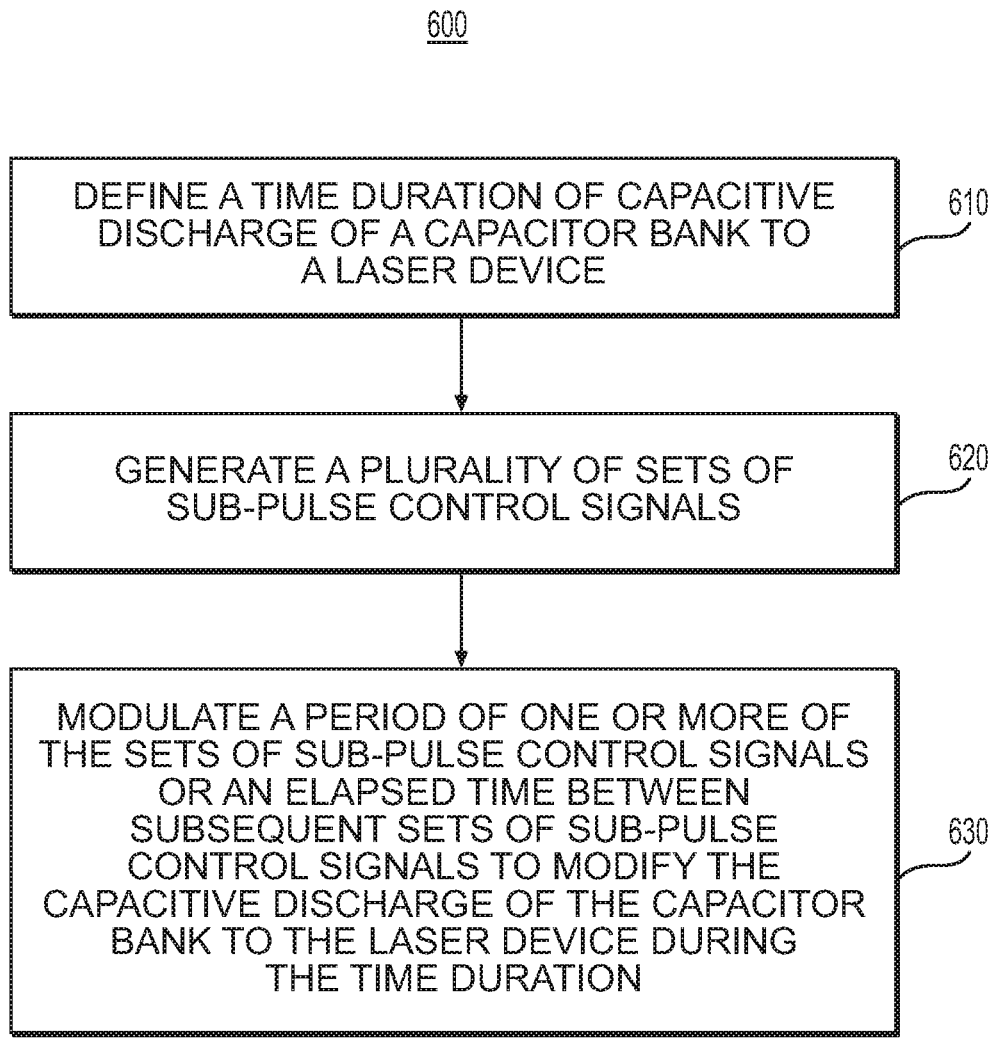
FIG. 6 shows a second example flow chart for controlling output laser pulse signals.

Reference is now made to FIG. 6, which shows a second example flow chart 600 for controlling output laser pulse signals. The operations in flow chart 600 may be performed by the control device 120. It should be appreciated that, as described above for FIG. 5, operations performed by the control device 120 in FIG. 6 may be similarly initiated or controlled by an operator of the control device 120. For example, the operations described in FIG. 6 may be performed at the instruction of the operator providing input signals to the control device 120 to perform the respective operations. In another example, the operations described in FIG. 6 may be performed automatically by the control device 120 based on the control device 120 receiving instructions about an intended or desired output signal from the operator. At 610, the control device 120 defines a time duration of capacitive discharge of an application of a control laser pulse signal to a laser device. As stated above in connection with FIG. 1, the control device 120 defines the time duration of the capacitive discharge based on the intended output laser pulse signal (e.g., the laser energy output) desired for the medical device 100 to treat the target 185. At 620, the control device 120 generates a plurality of sets of sub-pulse control signals, each of which defines a corresponding capacitive discharge event from the capacitor bank 140. The control device 120 sends the sub-pulse control signals to the modulator system 130, which operates the discharge of the capacitor bank 140 (e.g., by operating a switch interfaced with the capacitor bank 140) for a specified time defined by each of the sub-pulse control signals. At 630, the control device 120 modulates a period of one or more of the sets of sub-pulse control signals or an elapsed time between subsequent sets of sub-pulse control signals to apply the control laser pulse signal during the time period. The modulated signal is sent from the control device 120 to the modulator system 130 to modify/modulate the capacitive discharge of the capacitor bank 140.

Figure 7:
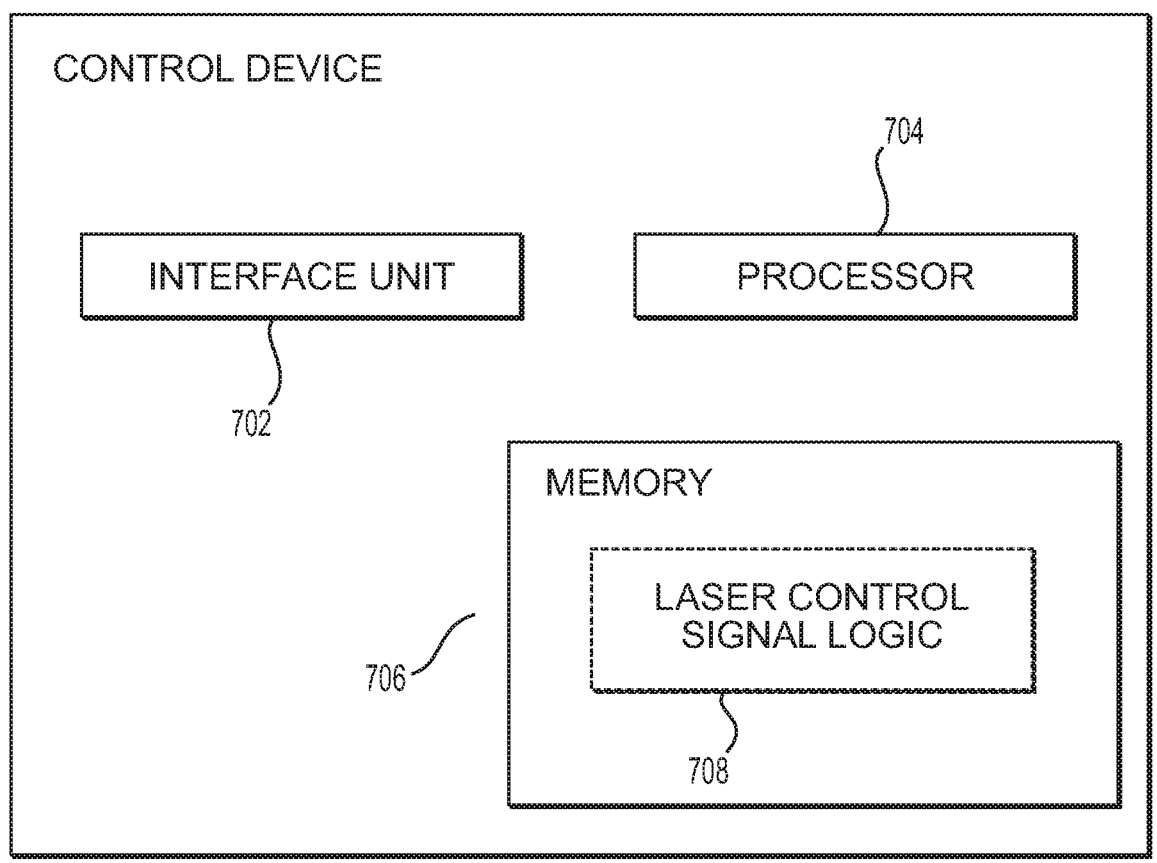
FIG. 7 shows an example computing device configured to perform the laser pulsing control techniques.

Reference is now made to FIG. 7, which shows a simplified functional block diagram of the control device 120. It should be appreciated that the control device 120 may be any computing device. The control device 120 may include an interface unit 702, a processor 704, and a memory 706. The interface unit 702 may be configured to send and receive signals (e.g., one or more of the control signals described herein to achieve a desired corresponding one or more output signals) to the modulator 130. For example, the interface unit 702 may send a plurality of sub-pulse control signals to modulator 130 over a network or through another data connectivity mechanism to instruct the modulator 130 to discharge the capacitor bank 140 according to the signal profile of the sub-pulse signals. The modulator 130 may receive the sub-pulse control signals from the interface unit 702 and may accordingly operate a switch interfaced with the capacitor bank 140 to discharge the capacitor bank for time durations specified by the sub-pulse control signals. The memory 706 may include laser control signal logic 708. The laser control signal logic 708 is configured to perform the laser pulsing control techniques, e.g., to generate laser pulsing control signals, as described by the techniques herein. The control device 120 also may include input and output ports to connect with input and/or output devices such as keyboards, mice, touchscreens, monitors, displays, etc. The various system functions described herein may be implemented in a distributed fashion on a number of similar platforms, to distribute the processing load. Alternatively, the systems may be implemented by appropriate programming of one computer hardware platform.

In one aspect, any of the disclosed systems, methods, and/or graphical user interfaces may be executed by or implemented by a computing system consistent with or similar to the descriptions herein. Although not required, aspects of the present disclosure are described in the context of computer-executable instructions, such as routines executed by a data processing device, e.g., a server computer, wireless device, and/or personal computer. Those skilled in the art will appreciate that aspects of the present disclosure may be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "computing device," and the like, are generally used interchangeably herein, and refer to any of the above devices and systems, as well as any data processor.

Aspects of the present disclosure may be embodied in a special purpose computer and/or data processor that is specifically programmed, configured, and/or constructed to perform one or more of the computer-executable instructions explained in detail herein. While aspects of the present disclosure, such as certain functions, are described as being performed exclusively on a single device, the present disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of the present disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer-implemented instructions, data structures, screen displays, and other data under aspects of the present disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit-switched, or other schemes).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors, or the like, or associated modules thereof, such as various semiconductor memories, tape drives, disk drives, and the like, which may provide non-transitory storage at any time for the software programming.

All or portions of the software may, at times, be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical, and electromagnetic waves, such as used across physical interfaces between local devices, through wired and optical landline networks, and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A method for controlling an output laser pulse signal of a medical device, the method comprising:
    at a control device, defining a time duration of capacitive discharge of a capacitor bank to a laser device, wherein the time duration corresponds to an intended energy of the output laser pulse signal;
    generating a pulse signal that defines a capacitive discharge event having a pulse width and a pulse period, wherein the pulse period is greater than the pulse width;
    generating a control laser pulse signal that defines a plurality of sub-pulse control signals, wherein each of the sub-pulse control signals includes a plurality of the pulse signals and wherein each of the plurality of sub-pulse control signals are separated by a burst delay, wherein the burst delay is different than the difference of the separation of the plurality of sub-pulse control signals; and
    modulating a duration of the burst delay to modify the capacitive discharge of the capacitor bank to the laser device during the time duration,
    wherein the aggregate of the elapsed time of the sub-pulse control signals and the burst delays equals the time duration defined by the control device.

2. The method of claim 1, wherein the sub-pulse control signal period corresponds to time elapsed between a start of the first sub-pulse control signal and a start of a subsequent sub-pulse control signal.

3. The method of claim 1, wherein the sub-pulse time duration corresponds to time elapsed between a start of a selected sub-pulse control signal and an end of the selected sub-pulse control signal.

4. The method of claim 1, further comprising controlling the output laser pulse signal by changing the time duration of the control laser pulse signal.

5. The method of claim 4, wherein changing the time duration of the control laser pulse signal comprises changing the time duration of the control laser pulse signal to increase a time width of a peak output value of the output laser pulse signal.

6. The method of claim 1 further comprising changing a frequency of the sub-pulse control signals to produce an output laser pulse signal with periodic peak output values.

7. The method of claim 1, wherein the sub-pulse control signals have a frequency of about 1 kHz to about 25 kHz.

* * * * *